United States Patent [19]

Brown

[11] 4,031,122
[45] June 21, 1977

[54] ARYLORGANOBROMOSILICONE COMPOUNDS

[75] Inventor: Paul L. Brown, Saginaw, Mich.

[73] Assignee: Dow Corning Corporation, Midland, Mich.

[22] Filed: Sept. 22, 1976

[21] Appl. No.: 725,219

[52] U.S. Cl. .................. 260/448.8 R; 252/8.6; 106/15 FP
[51] Int. Cl.² .................................. C07F 7/18
[58] Field of Search ....................... 260/448.8 R

[56] References Cited

UNITED STATES PATENTS

| 3,423,445 | 1/1969 | Holbrook et al. | 260/448.8 R X |
| 3,663,587 | 5/1972 | Holman | 260/448.8 R |

Primary Examiner—Paul F. Shaver
Attorney, Agent, or Firm—Jack E. Moermond

[57] ABSTRACT

Arylorganobromosilicone compounds having the general formula

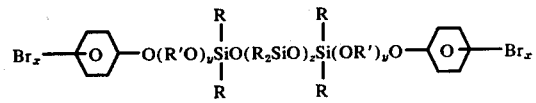

wherein $x$ has an average value of from 2 to 3, $R'$ is selected from the group consisting of ethylene, propylene and butylene radicals, $y$ has a value of from 1 to 10, $R$ is selected from the group consisting of hydrocarbon radicals containing from 1 to 18 carbon atoms, fluorinated hydrocarbon radicals containing from 1 to 18 carbon atoms, chlorinated hydrocarbon radicals containing from 1 to 18 carbon atoms and cyanohydrocarbon radicals containing from 1 to 18 carbon atoms, and $z$ has a value of from 0 to 25 are disclosed. These compounds are useful, for example, for improving the fire resistance of other materials.

7 Claims, No Drawings

ARYLORGANOBROMOSILICONE COMPOUNDS

The use of halogenated compounds of various kinds in flame-retardant applications is well documented in the literature. This is particularly true of the halogenated organic compounds.

The newly discovered arylorganobromosilicone compounds of this invention also find use in flame-retardant applications. Thus, the number of materials available to those working in the flame-retardant field has been significantly increased and makes it more feasible for them to match up the best materials for particular applications. Moreover, it is conceivable that the unique combination of the arylorganobromo moiety and the silicone moiety in the compounds of this invention will result in unusual properties in particular end uses.

More specifically, this invention relates to arylorganobromosilicone compounds having the general formula

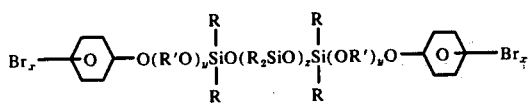

wherein $x$ has an average value of from 2 to 3, $R'$ is selected from the group consisting of ethylene, propylene and butylene radicals, $y$ has a value of from 1 to 10, $R$ is selected from the group consisting of hydrocarbon radicals containing from 1 to 18 carbon atoms, fluorinated hydrocarbon radicals containing from 1 to 18 carbon atoms, chlorinated hydrocarbon radicals containing from 1 to 18 carbon atoms and cyanohydrocarbon radicals containing from 1 to 18 carbon atoms, and $z$ has a value from 0 to 25.

As indicated above, $R'$ can be an ethylene, propylene or butylene radical or combinations thereof. Of these radicals the commercially available embodiments are preferred, with the ethylene radical being most preferred at this time. There can be from 1 to 10 of the $R'O$ units in each of the arylorganobromo moieties, i.e. $y$ can have a value of from 1 to 10. It is preferable, however, that the number of $R'O$ units be in the range of from 1 to 5.

Illustrative examples of the R radicals in the above formula include the methyl, ethyl, propyl, isopropyl, butyl, tertiary butyl, amyl, hexyl, octyl, 2-ethylhexyl, decyl, dodecyl, octadecyl, vinyl, allyl, hexenyl, dodecenyl, propargyl, cyclohexyl, phenyl, benzyl, tolyl, biphenylyl, naphthyl, 3,3,3-trifluoropropyl, 3,3,4,4,5,5,5-heptafluoropentyl, alpha,alpha,alpha-trifluorotolyl, perfluorocyclohexyl, 3-chloropropyl, 4-chlorobutyl, 2-cyanoethyl, 3-cyanopropyl, and 1,3-dicyanophenyl radicals. Of these radicals, the methyl and phenyl radicals are preferred at this time.

There can be from 0 to 25 of the $R_2SiO$ units in the compounds of this invention, that is, $z$ has a value from 0 to 25. It is believed, however, that the best flame-retardant properties can generally be obtained when $z$ has a value of from 0 to 8.

The compounds of this invention can be prepared by the reaction of an bromoarylcarbinol with an acetoxy endblocked siloxane in the presence of a suitable catalyst. This method will be illustrated in detail in the examples. Other methods by which the compounds of this invention can be prepared will be obvious to those skilled in the art.

The arylorganobromosilicone compounds of this invention can be applied to substrates to improve their fire resistance by any of the well known means such as by spraying, dipping, padding, nip roll and the like. The amount of the arylorganobromosilicone compound applied to the substrate will vary depending on the particular substrate and the effect desired. In some instances, it may be desired to incorporate these compounds directly into the substrate during formation. Generally speaking, however, the amount of the arylorganobromosilicone compound employed will be in the range of 0.1 to 5.0 percent by weight.

As noted above, the arylorganobromosilicone compounds of this invention can be applied to various substrates, particularly cellulosic substrates, to improve their flame retardant properties. Examples of such substrates include wood, jute, cotton, or hemp in the form of plywood panels, rope or textiles, for example, as well as to substrates made of nylon, polyamides, rayon or the like.

Now in order that those skilled in the art may better understand how the present invention can be practiced, the following examples are given by way of illustration and not by way of limitation. All parts and percents referred to herein are by weight and all viscosities are measured at 25° C. unless otherwise specified.

EXAMPLE 1

To a three-necked flask equipped with stirrer, condenser, dropping funnel, ammonia sparger and heating mantle there was added 188 g. of

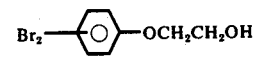

(composed of mono, di, and tri bromo substituted aromatic rings averaging two bromine atoms per molecule) and 200 ml. of a methoxy endblocked polyethylene glycol. The mixture was saturated with ammonia and then 106 g. of $CH_3COO[(CH_3)_2SiO]_3OCCH_3$ was slowly added while heating the mixture at 90° C. The amount of acetoxy endblocked siloxane was determined by following the reaction by gas-liquid chromotography (GLC) analysis. The heating completes the reaction more quickly. The salt (ammonium acetate) was washed from the mixture using two water washings. This caused little, if any, hydrolysis according to GLC analysis. The mixture was then stripped on a Rinco separator to obtain the solid product

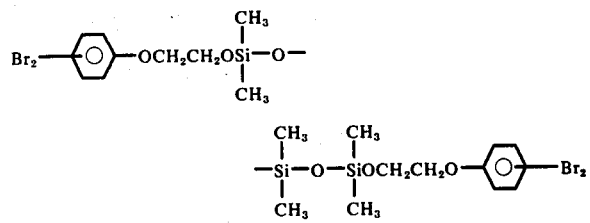

having a melting point of 26°–30° C.

EXAMPLE 2

The product of Example 1 was tested for flame resistant characteristics using the following tests.

Manifold Test

This test is the one described in Federal Test Methods No. 791A, Method 6053 "Manifold Ignition Test." In this test the test fluid is preheated to 450°±5° F. and then dropped at the rate of 100 drops per minute from a dropping funnel whose outlet is five inches above the center of the manifold. The surface temperature of the manifold is varied from 600° to 1200° F. in 100° increments. The minimum temperature at which the fluid burns is recorded.

Kim-Wipe Test

In this test a Kim-Wipe tissue is soaked with the test fluid. A bunsen burner is then held to the tissue for 5 seconds followed by cooling for 5 seconds, a total of 4 consecutive heating and cooling cycles being used.

Aluminum Dish Test

About 7 grams of the test fluid is placed in a small aluminum dish or cup in this test. The fluid is heated continuously with a bunsen burner to see if it will ignite or burn.

In the Manifold Test the test fluid ignited at about 1080° F. In the Kim-Wipe test the tissue did not burn. In the Aluminum Dish Test the test material did not burn after the flame was removed.

EXAMPLE 3

When the siloxanes and bromoarylcarbinols set forth below are substituted for their counterpart in Example 1 as the reactants in equivalent amounts, the indicated products are obtained.

(A) Siloxane: $CH_3COO[(CH_3)_2SiO]_2OCCH_3$

Bromoarylcarbinol: 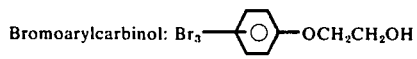

Product: 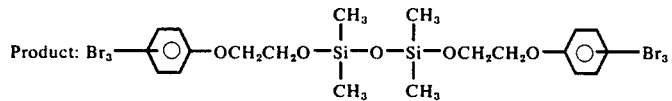

(B) Siloxane: $CH_3COO[(CH_3)C_6H_5SiO]_4OCCH_3$

Bromoarylcarbinol: 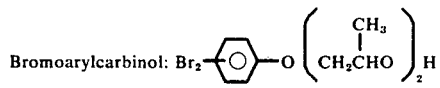

Product: 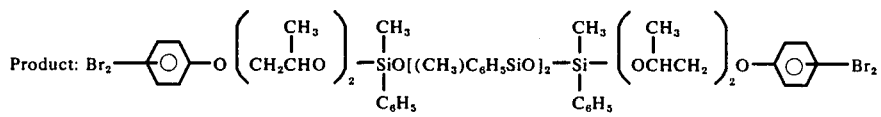

(C) Siloxane: $CH_3COO[(CH_3)_2SiO]_6[(CH_3)C_6H_5SiO]_2OCCH_3$

Bromoarylcarbinol: 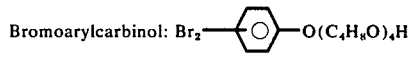

Product: 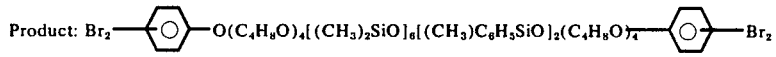

(D) Siloxane: $CH_3COO[(CH_3)CF_3CH_2CH_2SiO]_3OCCH_3$

Bromoarylcarbinol: 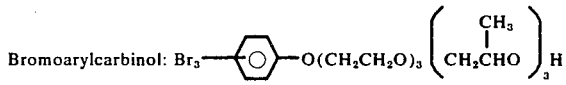

Product: 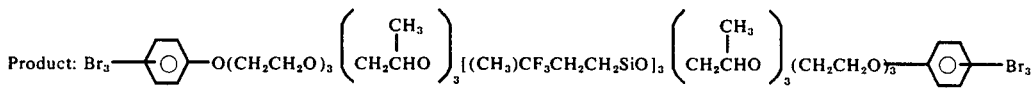

(E) Siloxane: $CH_3COO[(CH_3)_2SiO]_{25}OCCH_3$

Bromoarylcarbinol: 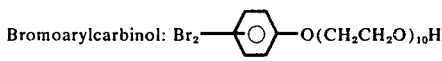

Product: 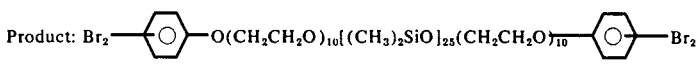

(F) Siloxane: $CH_3COO[(CH_3)ClCH_2CH_2CH_2SiO]_3OCCH_3$

Bromoarylcarbinol: 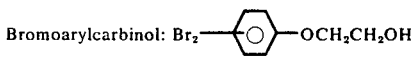

-continued

Product: $Br_2-\langle O \rangle-OCH_2CH_2O[(CH_3)ClCH_2CH_2CH_2SiO]_3CH_2CH_2O-\langle O \rangle-Br_2$ (G) Siloxane: $CH_3COO[(CH_3)NCCH_2CH_2SiO]_3OCCH_3$ Bromoarylcarbinol: $Br_2-\langle O \rangle-OCH_2CH_2OH$ Product: $Br_2-\langle O \rangle-OCH_2CH_2O[(CH_3)NCCH_2CH_2SiO]_3CH_2CH_2O-\langle O \rangle-Br_2$ That which is claimed is:

1. A silicone compound having the general formula $$Br_x-\langle O \rangle-O(R'O)_y\underset{R}{\overset{R}{Si}}O(R_2SiO)_z\underset{R}{\overset{R}{Si}}(OR')_yO-\langle O \rangle-Br_x$$

wherein
- $x$ has an average value of from 2 to 3,
- $R'$ is selected from the group consisting of ethylene, propylene, and butylene radicals,
- $y$ has a value of from 1 to 10,
- R is selected from the group consisting of hydrocarbon radicals containing from 1 to 18 carbon atoms, fluorinated hydrocarbon radicals containing from 1 to 18 carbon atoms, chlorinated hydrocarbon radicals containing from 1 to 18 carbon atoms and cyanohydrocarbon radical containing from 1 to 18 carbon atoms, and
- $z$ has a value of from 0 to 25.

2. A silicone compound as defined in claim 1 wherein R is a hydrocarbon radical.

3. A silicone compound as defined in claim 2 wherein R' is an ethylene radical and R is selected from the group consisting of methyl radicals and phenyl radicals.

4. A silicone compound as defined in claim 3 wherein $x$ has a average value of 2, $y$ has a value from 1 to 5 and $z$ has a value from 0 to 8.

5. A silicone compound as defined in claim 3 wherein $x$ has an average value of 3, $y$ has a value from 1 to 5 and $z$ has a value from 0 to 8.

6. A silicone compound as defined in claim 3 which has the general formula $$Br_x-\langle O \rangle-OCH_2CH_2O\underset{CH_3}{\overset{CH_3}{Si}}-O-$$

$$-\underset{CH_3}{\overset{CH_3}{Si}}-O-\underset{CH_3}{\overset{CH_3}{Si}}-OCH_2CH_2O-\langle O \rangle-Br_x$$

7. A silicone compound as defined in claim 6 wherein $x$ has an average value of about 2.

* * * * *

UNITED STATES PATENT AND TRADEMARK OFFICE
CERTIFICATE OF CORRECTION

PATENT NO. : 4,031,122
DATED : June 21, 1977
INVENTOR(S) : PAUL L. BROWN

It is certified that error appears in the above-identified patent and that said Letters Patent are hereby corrected as shown below:

Column 3, line 13, the title "Kim-Wipe Test" should read
--Kim-Wipe® Test-- .

Column 3, line 14, "Kim-Wipe" should read --Kim-Wipe®--.

Column 4, line 8, "Kim-Wipe" should read --Kim-Wipe®--.

Signed and Sealed this

Twenty-seventh Day of February 1979

[SEAL]

Attest:

RUTH C. MASON
Attesting Officer

DONALD W. BANNER
Commissioner of Patents and Trademarks